(12) United States Patent
Landau et al.

(10) Patent No.: US 7,881,874 B2
(45) Date of Patent: Feb. 1, 2011

(54) METHOD AND SYSTEM FOR COMPARATIVE GENOMICS

(75) Inventors: Gad M. Landau, Haifa (IL); Laxmi Priya Parida, Mohegan Lake, NY (US); Oren Weimann, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 1265 days.

(21) Appl. No.: 11/453,995

(22) Filed: Jun. 16, 2006

(65) Prior Publication Data

US 2007/0294038 A1  Dec. 20, 2007

(51) Int. Cl.
*G06F 19/00* (2006.01)
(52) U.S. Cl. .......................................... 702/19; 702/20
(58) Field of Classification Search ........................ None
See application file for complete search history.

(56) References Cited

PUBLICATIONS

Parida (IBM Research Report: A PQ Tree-based Framework for Reconstructing Common Ancestor under Inversions and Translocations (Dec. 23, 2005), Computer Science, IBM Research Division, Yorktown Heights, NY, pp. 1-14).*

Landau et al. (Lecture Notes in Computer Science: Using PQ Trees for Comparative Genomics. vol. 3537/2005, Springer Publication date of May 13, 2005, Springer Berlin in the book Combinatorial Pattern Matching, p. 128-143).*

Anne Bergeron, et al., "The Algorithmic of Gene Teams", WABI 2002, LNCS 2452, pp. 464-476, 2002.

Anne Bergeron, et al., "On the Similarity of Sets of Permutations and Its Applications to Genome Comparison", COCOON 2003, LNCS 2697, pp. 68-79, 2003.

Xin He, et al., "Identifying Conserved Gene Clusters in the Presence of Orthologous Groups", RECOMB'04, Mar. 27-31, 2004, pp. 272-280.

* cited by examiner

*Primary Examiner*—Lori A Clow
(74) *Attorney, Agent, or Firm*—McGinn IP Law Group, PLLC; Vazken A. Alexanian (57) ABSTRACT

A method and system for representing a similarity between at least two genomes that includes detecting gene clusters which are common to the at least two genomes and representing the common gene clusters in a PQ tree. The PQ tree includes a first internal node (P node), that allows permutation of the children thereof, and a second internal node (Q node), that maintains unidirectional order of the children thereof.

7 Claims, 10 Drawing Sheets

METHOD AND SYSTEM FOR COMPARATIVE GENOMICS

BACKGROUND OF THE INVENTION

1. Field of the Invention

The present invention generally relates to methods and systems for performing comparisons of genomic data. In particular, the present invention relates to methods and systems for providing a PQ tree that represents gene clusters that are common to at least two genomes.

2. Description of the Related Art

Genomes are sequences of genes. The inventors have multiple sets of genomes for which the inventors desired to study the similarity across these genomes. There is a theory that there is commonality across genomes due to a common origin. Genomes may be related to each other through a common ancestry.

Further, it is desirable to know the order of the ancestry for these genomes. The genomes, which were intermediates to the common origin and the current set of genomes, may not be known.

If a collection of genes in one genome appear together in another genome, there is a theory that these genomes are similar and that they may have a common ancestor.

Given two permutations of n distinct characters, a common interval may be defined to be a pair of intervals of these permutations consisting of the same set of characters, and an O(n+K) time algorithm for extracting all common intervals of two permutations may be devised, where:

$$K \le \binom{n}{2} \quad (1)$$

is the number of common intervals.

An O(n) type algorithm is an algorithm for which the amount of time it takes to solve the algorithm is directly proportional to the size of the input.

This may be extended to k sequences and presented an O(nk+K) time algorithm for extracting all common intervals of k permutations. The characters here represent genes and the string of characters represents the genome.

A "consecutive" constraint may be relaxed by introducing gene teams—allowing genes in a cluster to be separated by gaps that do not exceed a fixed threshold and an $O(kn \log^2 n)$ time algorithm may be used for finding all gene teams.

A conventional technique for deciding whether two genes are similar uses the biological concept of orthologs and paralogs. Two genes are matched if they are either orthologous (appear in different organisms, but have the same evolutionary origin and are generated during speciation) or paralogous (appear in the same organism and caused by the duplication of ancestor genes).

A slightly modified conventional model of a genome sequence, that allows paralogs extended a previous conventional model by representing genomes as sequences rather then permutations, and provides a $\Theta(n^2)$ algorithm for extracting all common intervals of two sequences.

The notion of gene teams may be extended to cluster of orthologous group (COG) teams by allowing any number of paralogs and orthologs, and an O(mn) time algorithm was devised to find such cluster of orthologous group teams for pairwise chromosome comparison (where m and n are the number of orthologous genes in the two chromosomes).

Pattern discovery has conventionally been formalized as a r-pattern problem. Let the pattern $P=p_1 \ldots p_m$ and the string $S=s_1 \ldots s_n$ both be sequences of characters (with possible repeats) over a given alphabet $\Sigma$ (in our case genes). P appears in location i in S iff $(p_1, \ldots, p_m)$ is a permutation of $(s_i, s_{i+1}, \ldots, s_{i+m-1})$. P is a $\pi$-pattern if it appears at least K times in S for a given K. A notation for maximal $\pi$-pattern was introduced as a model to filter meaningful from apparently meaningless clusters. A $\pi$-pattern $p_1$ is non-maximal with respect to $\pi$-pattern $p_2$, if each occurrence of $p_1$ is covered by an occurrence of $p_2$ and each occurrence of $p_2$ covers an occurrence of $p_1$. An algorithm works in two stages: In stage 1, all $\pi$-pattern of sizes $\le L$ are found in $O(Ln \log|\Sigma|\log n)$ time, where n is the total length of all the sequences. For every $\pi$-pattern found the algorithm stores a list of all the locations where the pattern appears, e.g., a location list. In stage 2, a straightforward comparison of every two location lists is used to extract the maximal $\pi$-pattern out of all the $\pi$-pattern found in stage 1. Assume stage 1 outputs p $\pi$-patterns, and the maximum length of a location list is l, stage 2 runs in $O(p^2 l)$ time. Integrating the two stages to produce only the maximal $\pi$-patterns was introduced as an open problem.

Conventional approaches output all the found patterns as sets of genes. These conventional approaches provide no knowledge of the ordering of the genes in each appearance of the pattern, and also outputs meaningless clusters.

SUMMARY OF THE INVENTION

In view of the foregoing and other exemplary problems, drawbacks, and disadvantages of the conventional methods and structures, an exemplary feature of the present invention is to provide methods and systems in which PQ trees are used for comparative genomics.

In a first exemplary aspect of the present invention, a method representing the similarities between at least two genomes includes detecting gene clusters, which are common to the two genomes, and representing the common gene clusters in a PQ tree. The PQ tree includes a first internal node (P node), that allows permutation of the children thereof, and a second internal node (Q node), that maintains unidirectional order of the children thereof.

In a second exemplary aspect of the present invention, a system for representing the similarities between at least two genomes includes a detector that detects gene clusters which are common to the two genomes, and a processor that represents the common gene clusters in a PQ tree. The PQ tree includes a first internal node (P node), that allows permutation of the children thereof, and a second internal node (Q node), that maintains unidirectional order of the children thereof.

In a third exemplary aspect of the present invention, a program embodied in a computer readable medium executable by a digital processing unit includes instructions for detecting gene clusters which are common to two genomes, and instructions for representing the common gene clusters in a PQ tree. The PQ tree includes a first internal node (P node), that allows permutation of the children thereof, and a second internal node (Q node), that maintains unidirectional order of the children thereof.

An exemplary embodiment of the present invention provides a new tool for representation and detection of gene clusters in multiple genomes, using a PQ tree. In this manner, the inner structure and the relations between clusters may be described succinctly.

Further, an exemplary embodiment of the present invention aids in filtering meaningful from apparently meaningless clusters and also gives a natural and meaningful way of visualizing complex clusters.

An exemplary embodiment of the present invention may provide a minimal consensus PQ tree that it is equivalent to a maximal π-pattern and each sub-graph of the PQ tree may correspond to a non-maximal permutation pattern.

An exemplary embodiment of the present invention handles multiplicity in permutations and also gives a linear time algorithm to construct the minimal consensus PQ tree.

The inventors demonstrate an exemplary embodiment of the present invention by providing results on whole genome data sets. By application of the exemplary embodiment on the whole genomes of human and rat the present invention found about 1.5 million common gene clusters but only about 500 minimal consensus PQ trees.

These and many other advantages may be achieved with the present invention.

BRIEF DESCRIPTION OF THE DRAWINGS

The foregoing and other exemplary purposes, aspects and advantages will be better understood from the following detailed description of an exemplary embodiment of the invention with reference to the drawings, in which.

DETAILED DESCRIPTION OF EXEMPLARY EMBODIMENTS OF THE INVENTION

Referring now to the drawings, and more particularly to FIGS. 1-14, there are shown exemplary embodiments of the method and structures of the present invention.

An exemplary embodiment of the present invention uses a PQ tree data structure to obtain the maximal notation of the appearances of a pattern in linear time.

A PQ tree is a type of tree data structure. A PQ tree is a rooted, labeled tree, with non-leaf nodes labeled P or Q. A P node has at least two children, and a Q node has at least three children. A PQ tree represents a set of possible orderings for the leaf nodes. The children of a P node can be reordered in any way. The children of a Q node can be put in reverse order. A PQ tree represents all leaf node orderings that can be achieved by any sequence of these two operations.

An exemplary embodiment of the present invention relies upon the following definitions.

Definition 1 (Maximal notation): Given k permutations on an alphabet Σ, representing k occurrences of a pattern. The maximal notation is obtained by using a '-' between two groups of one or more genes to denote that these groups appear as immediate neighbors in all the k permutations, and using a ',' otherwise.

Example 1

Consider the pattern {a, b, c, d, e, f} appearing once as abcdef and once as bdacfe, then the maximal notation of this pattern is ((a, b, c, d)-(e-j)).

There are two main reasons for obtaining the maximal notation:

(1). This notation provides knowledge of the inner structure of a pattern. ((a,b,c,d)-(e-f)) shows that e appears always adjacent to f and they both appear always adjacent to the group {a, b, c, d}.

(2) This notation provides knowledge of the non-maximal relations between patterns, and may be used to filter meaningful from apparently meaningless clusters (non-maximal). ((a,b,c,d)-(e-j)) shows that the patterns $\pi_1$={e,f} and $\pi_2$={a, b,c,d} are non-maximal w.r.t the pattern $\pi_3$={a,b,c,d,e,f}. Thus ((a,b,c,d)-(e-f)) holds all the information of patterns $\pi_1$, $\pi_2$ and $\pi_3$.

Results. Exemplary theoretical results include: (a) a minimal consensus PQ tree is equivalent to a maximal π-pattern and each sub-graph of the PQ tree corresponds to a non-maximal permutation pattern, and (b) the maximal notation of a π-pattern p in O(nk) time is obtained, where k is the number of appearances of p and n is the number of characters in p.

In accordance with an exemplary embodiment of the present invention, in a genome model that allows only orthologous genes (all k sequences are permutations of {1, 2, ..., n}), the maximal notation of the entire π-pattern {1, 2, ..., n} is obtained.

In accordance with an exemplary embodiment of the present invention in a genome model that allows orthologous and paralogous genes (a gene may appear any number of times in a sequence, and may appear in only some of the sequences) another gene clustering algorithm may find the π-pattern p.

An exemplary embodiment of the present invention obtains the maximal notation of p, and uses an $O(nk^2)$ time algorithm that finds all maximal π-patterns in the genome model that allows orthologous genes as well as genes that do not appear in all the sequences.

This specification provides the experimental results that were obtained by applying exemplary embodiment of the present invention on whole genome data sets: (1) human and rat genomes and (2) *E Coli* K-12 and *B Subtilis* genomes. (3) Chloroplast genomes in the flowering plant family Campanulaceae.

An exemplary embodiment of the present invention reduces the number of clusters to be analyzed as well as helps in visualizing the internal structures of the clusters.

A PQ tree data structure may be used to solve a general consecutive arrangement problem. A general consecutive arrangement problem is defined as:

Given a finite set X and a collection I of subsets of X, does there exist a permutation π of X in which the members of each subset s of I appear as a consecutive substring of π?

There is an efficient algorithm (linear in the length of the input, $O(n^2)$ in our terms) that solves this problem using a PQ tree. A PQ tree is a rooted tree whose internal nodes are of two types: P and Q.

The children of a P-node occur in no particular order while those of a Q-node appear in a left to right or right to left order. FIGS. 1-7 designate a P-node by a circle and a Q-node by a rectangle. The leaves of T are labeled bi-jectively by the elements of X. The frontier of a tree T, denoted by F(T), is the permutation of X obtained by reading the labels of the leaves from left to right.

Definition 2 (Equivalent PQ trees): Two PQ trees T and T' are equivalent, denoted T≡T', if one can be obtained from the other by applying a sequence of the following transformation rules:

(1) Arbitrarily permute the children of a P-node, and
(2) Reverse the children of a Q-node.

Any frontier obtainable from a tree equivalent with T is considered consistent with T, and C(T) is defined as follows: C(T)={F(T')|T≡T'}. We accordingly define the number of frontiers obtainable from a tree equivalent with T to be |C(T)|.

Clearly the equivalence relation is reflexive, symmetric and transitive. To make it computationally straightforward, an exemplary embodiment of the present invention uses a slightly stricter version of a PQ tree called the canonical PQ tree.

Definition 3 (Canonical PQ tree): A PQ tree that has no node with only one child and no P-node with only two children.

Note that it is straightforward to convert any PQ tree to its canonical form: a node with a single child is merged with its immediate predecessor. This process is continued until no such node remains. Further, any P node with exactly two children is changed to a Q node.

Through the rest of the present specification, the inventors assume a PQ tree is a canonical PQ tree. Some PQ trees are given special names:

Given a finite set X, the PQ tree having a single P node with X children that are all leaves is called the universal PQ tree. We denote the universal tree as Tu. Another important PQ tree is the null tree, which has no nodes at all. By convention the null tree has no frontier and its set of consistent permutations is empty.

An efficient algorithm for a REDUCE( ) function is defined below.

Definition 4 (REDUCE (I, T')): Given a collection I of subsets of N={1, 2, . . . , n} and a PQ tree T' whose leaves are {1, 2, . . . , n}, the function REDUCE(I, T) builds a PQ tree T' such that f is in C(T) iff f is in C(T') and every i in I appears as a consecutive substring of f.

The procedure REDUCE(I, T') will return the null tree if no frontier f in C(T') is such that every i in I appears as a consecutive substring of f. Note that if Tu is the universal PQ tree, then REDUCE (I, Tu) builds a PQ tree T such that f is in C(T) iff every i in I appears as a consecutive substring off. If the number of subsets in I≦n, as in our case, then the time complexity of REDUCE (I, Tu) is $O(n^2)$.

Below, the present specification presents an O(n) time complexity algorithm for the REDUCE function when I is a set of at most n intervals.

The following observation is immediate from the definition of the REDUCE( ) function. Informally, it says that if T is the PQ tree returned by REDUCE(I,Tu) then if we add more subsets of N to I then |C(T)| gets smaller.

Observation 1: Given two collections I1, I2 of subsets of N, if I1 ⊆ I2 and T1=REDUCE(I1,Tu) and T2=REDUCE(I2, Tu) then C(T2)⊆C(T1).

The inventors define a minimal consensus PQ tree as a representation of the maximal notation of the k occurrences of a π-pattern. Throughout the remainder of the present specification, the inventors define Π to be a set of k permutations π1, π2, . . . , πk representing k occurrences of a π-pattern N={1, 2, . . . , n}.

Definition 5 (Notation of a PQ tree): The notation of a PQ tree is obtained by writing the PQ tree as a parenthesized string with different symbols encoding P (comma separators) and Q (dash separators) nodes.

Figure 1:
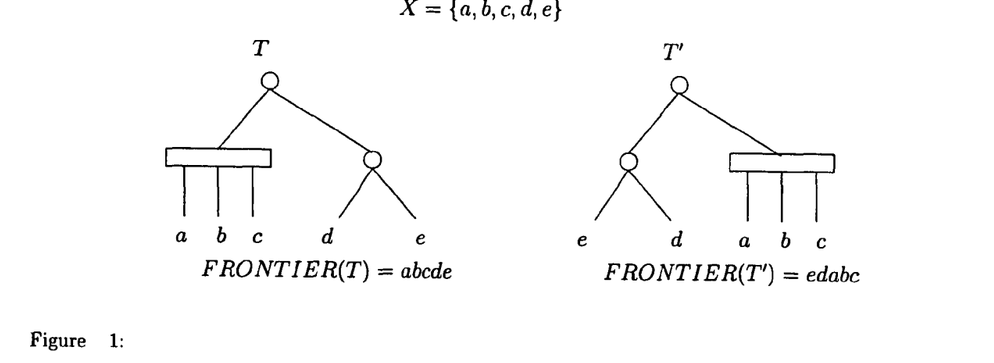
FIG. 1 illustrates two equivalent PQ trees, T'=T and their frontiers.
Figures 2, 3:
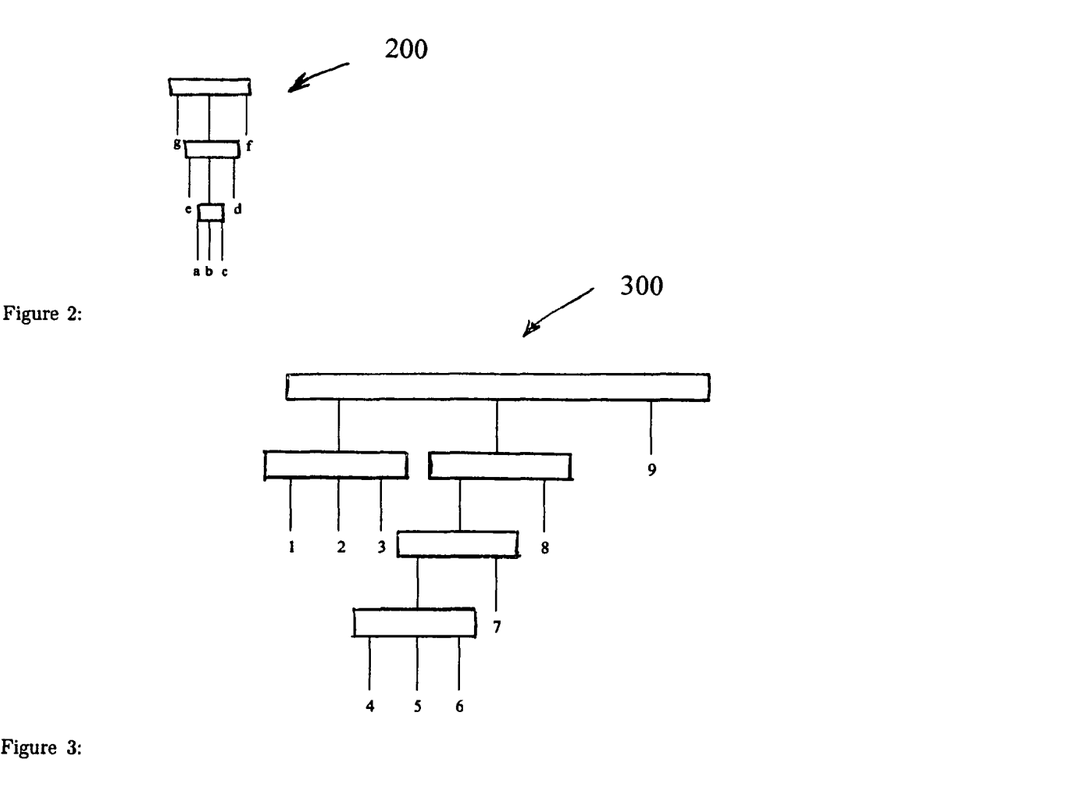
FIG. 2 shows a PQ tree 200 that illustrates a motivation for the definition of minimal consensus.
FIG. 3 illustrates an example of common intervals and a minimal consensus PQ tree 300.

For example in FIG. 1, T is denoted as ((a-b-c), (d, e)) and the PQ tree in FIG. 2 is denoted as (g-(e-(a-b-c)-d)-f). Given Π, our main goal is to construct a PQ tree T from Π, such that the notation of T is the maximal notation of Π.

FIG. 1 illustrates two equivalent PQ trees, T'≡T and their frontiers.

Note that C(T)=C'(T)={abcde, abced, cbade, dbaed, deabc, decba, edabc, edcba}.

We would like to construct a PQ tree T such that C(T)={π1, π2, . . . , πk} however, this is not always possible. Consider a π-pattern {a,b,c,d,e} appearing four times as abcde, abced, cbade, edabc, the PQ tree T in FIG. 1 is the one that best describes these appearances. However, edcba is in C(T) although the π-pattern never appeared as edcba. On the other hand, notice that the universal PQ tree over Σ, Tu, is such that {π1, π2, . . . , πk}⊆C(Tu). Hence the idea of minimal is introduced.

The present specification next presents a way of relating a set of permutations to a PQ tree.

Definition 6 (minimal consensus PQ tree): Given Π, A consensus PQ tree T of Π is such that Π CC(T) and the consensus PQ tree is minimal when there exists no T'≠T such that Π⊆C(T') and |C(T')|<|C(T)|.

FIG. 2 shows a PQ tree 200 that illustrates the motivation for the definition of minimal consensus. By defining the minimal consensus PQ tree, the problem now is to devise a method to construct the minimal consensus PQ tree given Π. Later the specification explains that the notation of the minimal consensus PQ tree of Π is the maximal notation of Π.

For FIG. 2, let c1=geabcdf and c2=fecbadg. The PQ tree 200, T in FIG. 2, is a minimal consensus PQ tree of {c1, c2}.

Definition 7 (Common Interval (CΠ)): Given Π, w.l.o.g we assume that π1:=(1, 2, . . . , n). An interval [i,j] (0<i<j<n+1) is called a common interval of Π iff the elements of the set {i,i+1, . . . ,j} appear as a consecutive substring in every πi in Π (i=1, 2, . . . , k). The set of all common intervals of Π is denoted CΠ.

See FIG. 3 for an example of common intervals and a minimal consensus PQ tree 300. FIG. 3 illustrates a minimal consensus PQ tree 300 of Π={π1. π2, π3} where π2=(1, 2, 3, 4, 5, 6, 7, 8, 9), π2=(9, 8, 4, 5, 6, 7, 1, 2, 3), and π3=(1, 2, 3, 8, 7, 4, 5, 6, 9). The maximal notation of the PQ tree is ((1-2-3)-(((4-5-6)-7)-8)-9).

The present specification now presents some theorems leading up to the uniqueness of a minimal consensus tree.

Theorem 1. Given Π, TC=REDUCE(CΠ, Tu) is a minimal consensus PQ tree of Π.

The following corollary is immediate from the proof of Theorem 1.

Corollary 1. If T1 and T2 are two minimal consensus PQ trees of Π, then C(T1)=C(T2).

Theorem 2. For two PQ trees T1 and T'2, if C(T1)=C(T'2), then T1≡T'2.

The following corollary is straightforward to verify.

Corollary 2. Given Π, the minimal consensus PQ tree T of Π is unique (up to equivalence).

The minimal consensus PQ tree is not necessarily unique when a character can appear more than once in a π-pattern. The inventors explain how to handle this problem in detail below.

A PQ subtree is a method for identifying non-maximal permutation patterns, and the inventors make the simplifying assumption that there are no multiplicities in the π-patterns, this problem is addressed in detail below.

Definition 8 (PQ subtree): Given a PQ tree T, the variant v' of a node v is defined as follows:

(1) If v is a P node then it's only variant v' is the P node itself
(2) If v is a Q node with k children, then a variant v' of v is a Q node with any k'≤k consecutive children of v.

A PQ subtree is rooted at a variant v' of node v and includes all its descendants in the PQ tree T Let L(v') denote the set of the labels of the leafnodes reachable from v'. Further, given the leafnode labels p=α1, α2, . . . , αn), the least common ancestor (LCA) of p is that variant v' of a node v satisfying the following:

(1) p⊆L(v) and (2) there exists no variant v'' of v or any other node such that p⊆L(v'') and |L(v'')|<|L(v')|.

Recall that a π-pattern p1 is non-maximal with respect to π-pattern p2, if each occurrence of p1 is covered by an occurrence of p2 and each occurrence of p2 covers an occurrence of p1.

One may assume that p1={α1, α2, . . . ,αn} and p2 are π-patterns such that p1 is non-maximal with respect to p2. The inventors denote Ti as the minimal consensus PQ tree of the appearances of π-pattern pi, and CΠi as the set of all common intervals of the occurrences of pi. The following definition will aid in describing the connection between PQ subtrees and non-maximal π-patterns (Theorem 3)

Definition 9 (Ti^pj): Given a PQ tree Ti, and a π-pattern pj={α1,α2,...,αn}, let v' be the LCA of pj in Ti. Then Ti^pj is the PQ subtree rooted at v'.

Theorem 3. Given πpatterns p1, p2 on some S if p1 is non-maximal w.r.t p2 then T2^p1≡T_1.

The following two lemmas prove theorem 3.

Lemma 1. CΠ1 $\hat{\subset}$ CΠ2.

Lemma 2. The leaves of T2^p1 are exactly p1={α1, α2, . . . , αn}.

Notice that the converse of Theorem 3 is true only if every occurrence of p1 is covered by an occurrence of p2. In an exemplary embodiment this property holds since the embodiment deals with π-patterns that appear exactly once in each of the k sequences.

The following theorem proves that given Π, the problem of obtaining the maximal notation of Π is equivalent to the problem of constructing the minimal consensus PQ tree of Π.

Theorem 4. The notation of the minimal consensus PQ tree of a πpattern is the maximal notation of the π-pattern.

Given Π, it is desirable to construct a PQ tree T such that C(T)=Π. However, as shown earlier this is not always possible using a PQ tree. This requires more precise definitions of the P and the Q node. Adding restrictions to the PQ tree will help solve the problem.

The inventors suggest the following: (1) Assigning a bi-directional annotation to the Q node as⇐only when the children appear in both directions in the strings and un-annotated otherwise. (2) The exact permutations appearing in the strings for the P node.

For example if a P node has 7 children and the annotation is (3162574, 5142736), then this implies that the P node has three possible permutations on it's children as 1234567, 3162574, and 5142736. Note that the children are not necessarily leaf nodes. See FIG. 4 for an example.

Figure 4:
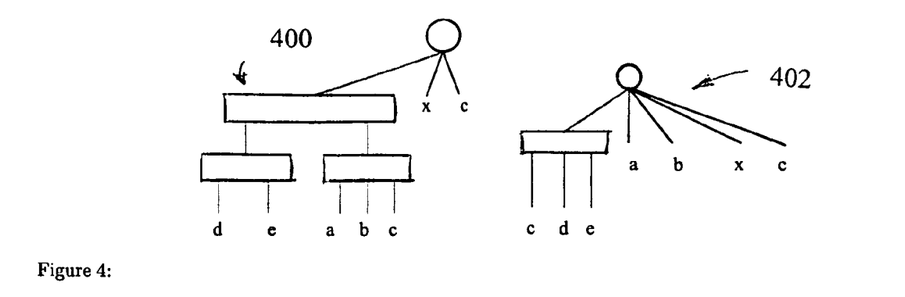
FIG. 4 illustrates a PQ tree 400 on the left, T1 and a PQ tree 402 on the right, T2.

FIG. 4 illustrates a PQ tree 400 on the left T1 and a PQ tree 402 on the right T2. Consider two permutations C1=abcdexc and c2=cdeacbx. Notice that c1, c2∈C(T1), C(T2). Let c3=deabcxc, c4=cdeabxc. Then c3∈T1, c3∉T2 and c4∈T2, c4∉T1. Thus, C(T1) X C(T2) and C(T2) X C(T1). So, both T1 and T2 are minimal but not equivalent.

The advantage of this is that the PQ tree remains the same and the annotations simply help remove the extra frontiers, C(T)\Π, where T is the un-annotated PQ tree.

The inventors devised new algorithms for computing the minimal consensus PQ tree. The first algorithm runs in O(kn+n$^2$) time. The inventors then improved this algorithm to O(kn) time, which is optimal since the length of the input is kn.

First, find a subset of CΠ of size O(n) that holds sufficient information about the k permutations. For example, consider the π-pattern {1, 2, 3} appearing twice as Π={123,321}, then CΠ={[1,2],[2,3],[1,3]}.

In Theorem 1 we proved that the minimal consensus PQ tree T is such that in every f in C(T) the sets {1,2}, {2,3} and {1,2,3} appear as a consecutive substring. Notice that the common interval [1,3] is redundant in the sense that if the sets {1,2} and {2,3} appear as a consecutive substring in every f in C(T), then {1,2,3} must also appear as a consecutive substring in every f in C(T).

The common interval [1,3], which is the union of [1,2] and [2,3], is therefore not necessary for constructing T.

The inventors next show that the set of common intervals that are necessary for constructing T is the set of irreducible intervals. Given Π, without loss of generality, it is assumed that π1:=(1, 2, . . . , n). Two common intervals c1, c2 both in CΠ have a non-trivial overlap if c1∩c2≠{ } and they do not include each other. A list p=(c1, c2, . . . , clp) of common intervals c1, c2, . . . , clp (all in CΠ) is a chain (of length lp) if every two successive intervals in p have a non-trivial overlap. A chain of length one is called a trivial chain. A common interval I is called reducible if there is a non-trivial chain that generates it (I is the union of all elements in all the intervals of the chain), otherwise it is called irreducible. This partitions the set of common intervals CΠ into the set of reducible intervals and the set of irreducible intervals, denoted IΠ. Obviously:

$$1 \le |I\Pi| \le |C\Pi| \le \binom{n}{2} \quad (2)$$

Figure 5:
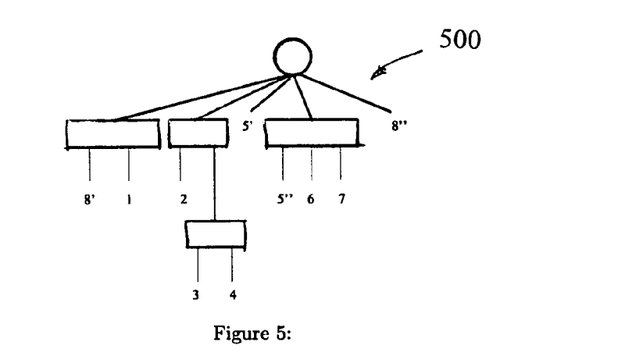
FIG. 5 illustrates the final data structure 500, S of the example of FIG. 3.

The set of irreducible common intervals of H from the example in FIG. 3 is:

$$I\Pi=\{[1,2],[1,8],[2,3],[4,5],[4,7],[4,8],[4,9],[5,6]\} \quad (3)$$

and their chains are illustrated in FIG. 5.

Consider two sequences 1234567 and 1824376, after tagging and adding characters, we get two permutations of 8'12345'5"678" and 5'18'8"243765', the minimal consensus tree is illustrated in FIG. 5. The sub-trees that have no tagged elements (notated (2-(3-4)) and (6-7)) are the only maximal π-patterns of the original sequences.

An exemplary embodiment of the present invention takes advantage of the fact that the irreducible intervals hold as much information as CΠ.

PQ-Construct:

Input: Π.

Output: The minimal consensus PQ tree T of Π.
  Compute IΠ using the algorithm described in [HS01].
  Compute T=REDUCE(IΠ, Tu)—Return T.
  In Theorem 1, the inventors proved that Tc=REDUCE(CΠ, Tu) is the minimal consensus PQ tree of Π. In the following theorem, the inventors prove that if TI=REDUCE(IΠ,Tu) then Tc=TI, thus proving the correctness of the invention.
  Theorem 5. Given Π, TI=REDUCE(IΠ, Tu) is the minimal consensus PQ tree of Π.

Time complexity of the invention. Given k permutations each of length N, by [HS01], |IΠ|<n and further, IΠ can be computed in O(kn) time. Computing T=REDUCE(IΠ,Tu) takes $O(n^2)$ time. The minimal consensus PQ tree can therefore be computed in $O(kn+n^2)$ time.

For the following portion of the detailed description, the inventors modify step 2 of the PQ-Construct algorithm to run in O(n) time. Conventionally, a data structure S was used to obtain the irreducible intervals. For each chain of non-trivially overlapping irreducible intervals, S contains a doubly-linked list that holds the intervals of that chain in left-to-right order. Moreover, intervals from different lists with the same left or right end are connected by vertical pointers yielding for each index x in N a doubly-linked vertical list. The final data structure 500, S of the example in FIG. 3 is shown in FIG. 5.

An exemplary embodiment of the present invention uses a new procedure called REPLACE(S) that transforms S to the minimal consensus PQ tree. The general idea is to replace every chain by a Q node where the children of the Q node are the roots of subtrees with leaves induced by the intersection between the intervals of the chain.

For example, in FIG. 5 the chain ([1,8],[4,9]) is replaced by a Q node of three children where each child is the root of a subtree containing the leaves {1,2,3}, {4,5,6,7,8} and {9} respectively. Then every element that is not a leaf or a Q node and is pointed by a vertical link is replaced with a P node.

For example, in FIG. 5 the vertical links from [4,8] to [4,7] and 8 implies that [4,8] is replaced by a P node with two children where each child is the root of a subtree containing the leaves {4,5,6,7} and {8} respectively.

Finally, a P node with 2 children is replaced by a Q node. The PQ tree 300 obtained by REPLACE(S) is illustrated in FIG. 3.

The following theorem proves that an exemplary embodiment of the present invention obtains the minimal consensus PQ tree using REPLACE(S).

Theorem 5. REPLACE(S)=REDUCE(IΠ,Tu).

Time complexity of the algorithm. IΠ and S can be computed in O(kn) time.

REPLACE can be performed by a simple bottom up traversal of S, therefore in O(n) time. The minimal consensus PQ tree can therefore be computed in O(kn) time.

The present specification now presents three different genome models that use the PQ tree tool to detect and represent the maximal patterns as PQ trees.

The first model allows only orthologous genes (all the k sequences are permutations of the same N genes, thus, every gene appears exactly once in every sequence).

The second model allows both orthologous and paralogous genes (a gene may appear any number of times in a sequence, and may appear in only some of the sequences).

The third allows orthologous genes as well as genes that do not appear in all the sequences (a gene can appear at most once in a sequence).

(1) Genomes as Permutations with no Multiplicity. This model is ideal for an exemplary embodiment of the present invention. Since the k sequences are permutations of Σ with no multiplicity, Σ is a π-pattern common interval) of size N.

Furthermore, it is the only maximal π-pattern in the sequences. An exemplary embodiment of the present invention constructs the minimal consensus PQ tree, T, of the set of sequences and obtain the maximal notation of the only maximal π-pattern in O(kn) time. Notice that by traversing T, all the π-patterns (common intervals) of the sequences (every subtree of T is a π-pattern) in O(K) time can be outputted, where $$K \le \binom{n}{2}$$

is the number of π-patterns. Therefore, in O(nk+K) time we can output all the non-maximal π-patterns.

An exemplary embodiment of the present invention also presents the maximal notation of every π-pattern found, and presents the non-maximal relations between them.

The present specification now illustrates application of an exemplary embodiment of the present invention to compare human and rat whole genome data.

(2) Genomes as Strings with Multiplicity.

In this case the input is a set of k sequences of N genes, where a gene can appear K times.

A string that has at least one character that appears more than once is termed as a string with multiplicity. For example if p1=abcegd and p2=acgcab, then p1 has no multiplicity. However that is not the case with p2 where a and c each appear more than once.

Consider a pattern p with occurrences as acbdefc and cdabfec. Clearly, p has a unique minimal consensus PQ tree corresponding to acbdefc' and cdabfec' and treating c' as a distinct character. However, the minimal consensus PQ tree is not necessarily unique when a character can appear more than once in a πpattern. This is illustrated in an example in FIG. 6.

Figure 6:
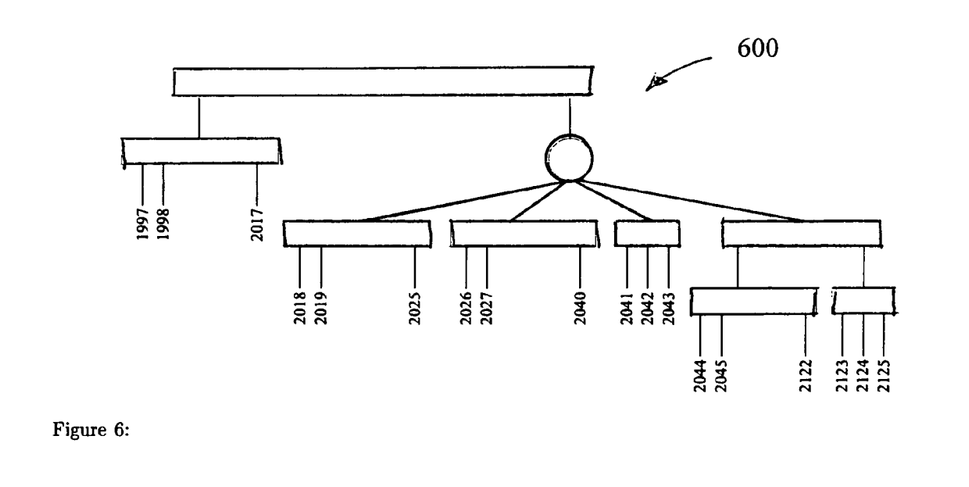
FIG. 6 illustrates a PQ sub-tree 600 of the minimal consequence PQ tree of the human genome and the rat genome orthologous genes.

FIG. 6 illustrates A PQ sub-tree 600 of the minimal consequence PQ tree of the human genome and the rat genome orthologous genes, as predicted by SLAM (a tool for Cross-Species Gene Finding and Alignment with a Generalized Pair Hidden Markov Model). The PQ tree 600 is: (((1997-1998- . . . -2017)-((2018-2019- . . . -2025),(2026-2027-. . .-2040),(2041-2042-2043),((2044-2045-. . .-2122)-(2123-2124-2125))))).

An exemplary embodiment of the present invention handles multiplicity by reporting the multiple minimal consensus PQ trees. This is explained using the example of FIG. 6. Each character is labeled with a distinct integer in the reference sequence and the remaining sequences are treated as multi-sets (strings of sets of characters). In the example, p1=deabcxc=1234567 and, p2=cdeabxc=[57]12346[57] and p3=cxcbaed=[57]6[57]4321. If Π1 and Π2 are two choices such that CΠ2 ⊂ CΠ1, then clearly the choice of Π1 is made over Π2. Continuing the example, the two choices for p2 are (1)p2=5123467, hence p3=5674321 or p3=7654321 so that [6,7] is in CΠ and (2)p2=7123465, hence p3=5674321 or p3=7654321 so that [5,6] is in CΠ. See FIG. 6 for the corresponding PQ tree 600.

Experimental results for this type of data are presented below, of a pairwise comparison between the genomes of E Coli K-12 and B Subtilis and of a comparison between thirteen chloroplast genomes in the flowering plant family Campanulaceae.

An exemplary embodiment of the present invention finds the π-patterns and present2 the maximal patterns as PQ trees (thus automatically filtering out the non-maximal patterns).

(3) Genomes as Strings with no Multiplicity. In this case, an exemplary embodiment receives a set of k sequences of N genes, where a gene can appear K<2 times. An $O(nk^2)$ time algorithm that finds all maximal π-patterns in the sequences (notice that there can now be more then one maximal π-pattern) may be used. The idea is to transform the sequences into permutations of the same set, and then build the minimal consensus PQ tree of these permutations.

Consider the following example, where there are two sequences, 1234567 and 1824376. First, tagging the genes that do not appear in all the sequences, results in 12345'67 and 18'24376. Then, replace every tagged gene g' with g'g" in the sequences where g' appears, and add g' in the beginning of the sequence and g" in the end of the sequence in the sequences where g' doesn't appear. That results in 8'12345'5"678" and 5'18'8"243765". Now, the tagged sequences are permutations of the same set, and furthermore, every π-pattern that appeared in all the original sequences, appears in the tagged sequences, and every π-pattern that appears in the tagged sequences but doesn't appear in the original sequences must contain a tagged element (this is achieved by splitting the tagged and double tagged elements).

Next, the embodiment constructs the minimal consensus PQ tree T of the tagged sequences. Notice that if a subtree Ti of T has no tagged leaves and there is no subtree Tj of T such that Ti is a subtree of Tj and Tj has no tagged leaves, then Ti represents a maximal π-pattern. The minimal consensus PQ tree 700 of the set of tagged sequences created from our example is shown in FIG. 7.

Figure 7:
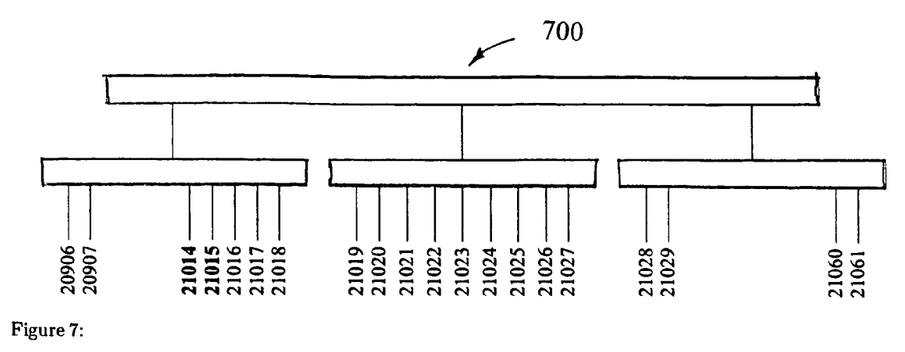
FIG. 7 illustrates a PQ tree 700 that is a PQ sub-tree of the minimal consensus PQ tree of the human genome and the rat genome orthologous genes.

FIG. 7 illustrates a PQ tree 700 that is a PQ sub-tree of the minimal consensus PQ tree of the human genome and the rat genome orthologous genes, as predicted by SLAM. The genes in bold are the functionally related genes PMP22 and TEKTIN3.

The present specification now explains the time complexity of an exemplary embodiment of the present invention. There are initially k sequences of length N each. In order to tag and add the elements as needed, for each element a list of the locations over all the sequences where this element appears is saved. In the worst case, every element appears in only one sequence and, thus, it takes $O(nk^2)$ time to tag and add the elements as needed. After the elements are tagged and added there are k tagged sequences of the same length (which is at most 2nk if every gene appears in only one sequence, which rarely happens). The minimal consensus PQ tree construction of the tagged sequences takes $O(nk^2)$ time using the O(nk) algorithm described above. Therefore, an exemplary embodiment of the present invention takes $O(nk^2)$ time.

Experimental results produced by an exemplary embodiment of the present invention for this type of data of a comparison between eight chloroplast genomes in the flowering plant family Campanulaceae are presented below.

The specification presents experimental results generated by an exemplary embodiment of the present invention for the three different genome models below.

Application of an exemplary embodiment of the present invention on E Coli K-12 and B Subtilis genomes found only about 450 minimal consensus PQ trees out of about 15,000 gene clusters, and when comparing eight different Chloroplast genomes the present invention found only 77 minimal consensus PQ trees out of about 6,700 gene clusters.

First, an exemplary embodiment of the present invention builds and analyzes the PQ tree of human and rat whole genomes. In order to build a PQ tree for whole genome comparisons this embodiment uses the output of a program called SLAM.

As explained above, SLAM is a comparative-based annotation and alignment tool for syntenic genomic sequences that performs gene finding and alignment simultaneously and predicts in both sequences symmetrically. When comparing two sequences, SLAM works as follows: Orthologous regions from the two genomes as specified by a homology map are used as input, and for each gene prediction made in the human genome there is a corresponding gene prediction in the rat genome with identical exon structure.

The inventors used the results from SLAM of comparing human (NCBI Build 31, November 2002) and rat (RGSC v2, November 2002) genomes, sorted by human chromosomes. The data in every chromosome is presented as a table containing columns: Gene name, rat coords, human coords, rat coding length, human coding length and #Exons.

There were 25,422 genes predicted by SLAM, each gene appears exactly once in each of the genomes. An exemplary embodiment of the present invention mapped every one of the 25,422 genes to an integer by mapping the first gene predicted by SLAM in human chromosome 1 (M4H1U1D4r106.002) to 1, the second (M4H1U1D4r106.001) to 2 and so on (after mapping chromosome 1 move to chromosome 2 and so on). Thus, the human genome becomes the identity permutation ($1, 2, 3, . . . , 25422$), and the rat genome becomes a permutation of {1, 2, 3, . . . , 25422} obtained from the SLAM output table.

Ignoring the trivial permutation pattern involving all the genes, there were only 504 interesting maximal ones out of 1,574,312 permutation patterns in this data set (we only consider patterns that do not cross chromosomes).

Figure 8:
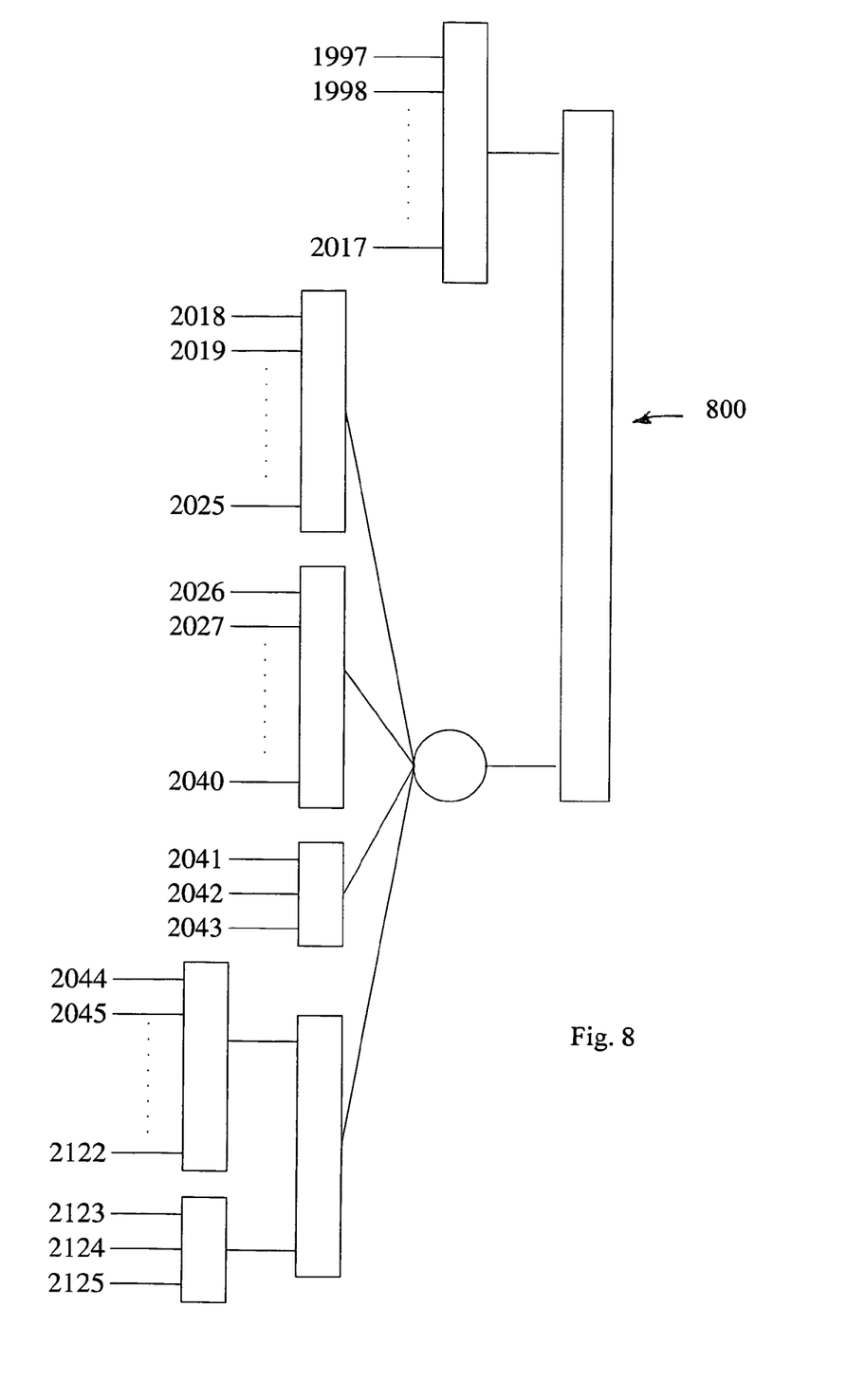
FIG. 8 illustrates a sub-tree 800 of the Human-Rat whole genome PQ tree in accordance with an exemplary embodiment of the present invention.

FIG. 8 illustrates a subtree 800 of the Human-Rat whole genome PQ tree. This tree corresponds to a section of 129 genes in human chromosome 1 (coordinates 203975896-217701720) and in rat chromosome 13 (coordinates 92630521-103808253).

By our mapping, these 129 genes appear in the human genome as the permutation: (1997-2125) and in the rat genome as the permutation: (2043-2041, 2025-2018, 2123-2125, 2122-2044, 2040-2026, 2017-1997). FIG. 8 is the minimal consensus PQ tree 800 of these two permutations.

Figure 9:
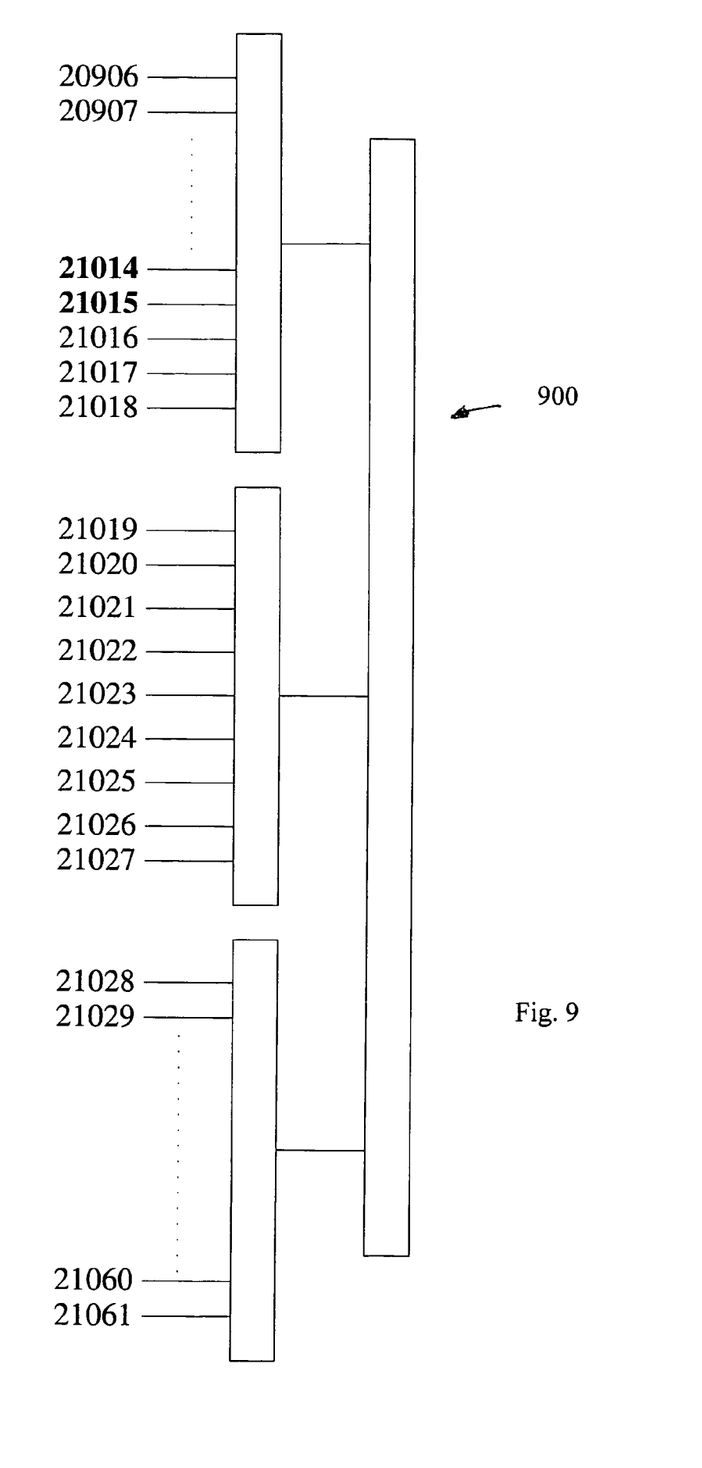
FIG. 9 illustrates another sub-tree 900 of the Human-Rat whole genome PQ tree in accordance with an exemplary embodiment of the present invention.

FIG. 9 illustrates another sub-tree 900 of the Human-Rat whole genome PQ tree. This tree corresponds to a section of 156 genes in human chromosome 17 (coordinates 7670777-21846001) and in rat chromosome 10 (coordinates 43816300-54626178).

By our mapping, these 156 genes appear in the human genome as the permutation: (20906-21061) and in the rat genome as the permutation: (21028-21061, 21019-21027, 21018-20906).

FIG. 9 is the PQ tree 900 of these two permutations. The two genes in bold represent genes PMP22 and TEKTIN3 (denoted M1H17U1 D5r2.002 and M11H17U1D5r2.001 respectfully in SLAM data). The PQ tree 900 of FIG. 9 clearly shows that these genes appear one next to the other both in human and in rat genomes, the reason for this is that they are indeed functionally related genes.

Note that the PQ tree 900 in FIG. 9 shows the notation of the 156-π-pattern {20906, 20907, 20908, . . . , 21061} which is (((20906-20907- . . . -21017-21018)- (21019-21020- . . . -21026-21027)- (21028-21029-21060-21061))).

The present specification describes below a simple, yet interesting PQ tree obtained from a pairwise comparison between the genomes of *E Coli* K-12 and *B Subtilis*. The input data was obtained from NCBI GenBank, in the form of the order of COGs (Clusters Of Orthologous Groups) and their location in each genome. All clusters of genes appearing in both sequences were extracted such that two genes are considered neighboring if the distance between their starting position on the chromosome (in bps) is smaller than a chosen parameter $\delta > 0$.

One experimental result, for $\delta = 1900$ was the detection of a cluster of only two genes: COG0718, whose product is an uncharacterized protein conserved in bacteria, and COG0353, whose product is a recombinational DNA repair protein. The function of COG0353 might give some clues as to the function of COG0718 (which is undetermined).

In an experiment, an exemplary embodiment of the present invention built PQ trees of clusters of genes appearing in both sequences, such that two genes are considered neighboring if they are consecutive in the input data irrespective of the distance between them. There were 450 maximal permutation patterns out of 15,000 patterns discovered by the present invention.

A particularly interesting cluster is (COG2812-COG0718-COG0353). The product of COG2812 is DNA polymerase III, is also related to DNA repair. The PQ tree clearly shows that COG0718, whose function is undetermined is located between two genes whose function is related to DNA repair. This observation further contributes to the conjecture that the function of COG0718 might be also related to DNA repair. Note that the reason that COG2812 was not clustered with COG0718 and COG0353 conventionally is because the distance between the starting locations of COG2812 and COG0718 is 1984 ($>\delta 1900$).

Chloroplast DNA gene order changes have been useful in phylogenetic reconstruction in many plant groups. These changes have considerable potential to resolve phylogenetic relationships and they provide valuable insights into the mechanisms of cpDNA evolution [CJMRWWW00].

The inventors below present a minimal consensus PQ tree obtained from a comparison between thirteen chloroplast genomes in the flowering plant family Campanulaceae: *Trachelium, Campanula, Adenophora, Symphyandra, Legousia, Asyneuma, Triodanus, Wahlenbergia, Merciera, Codonopsis, Cyananthus, Platycodon*, and Tobacco.

An exemplary embodiment of the present invention discovered 167 maximal permutation patterns out of 10,769 patterns. This embodiment presents the minimal consensus PQ tree of the π-pattern {1, 2, . . . , 54, 54, 55, 55, 56, . . . , 105} that appears in two out of the thirteen chloroplast genomes as the following permutations:

In *Campanula*: (1-15,76-49,39-37,40,35-26,44-41,45-48, 36,25-16,90-84,77-83,91-96,55-54,105-97).

In *Wahlenbergia*: (1-11,60-49,37-40,35-28,12-15,76-61, 27-26,44-41,45-48,36,54,25-16,90-84,77-83,91-96,55,105-97).

Figure 10:
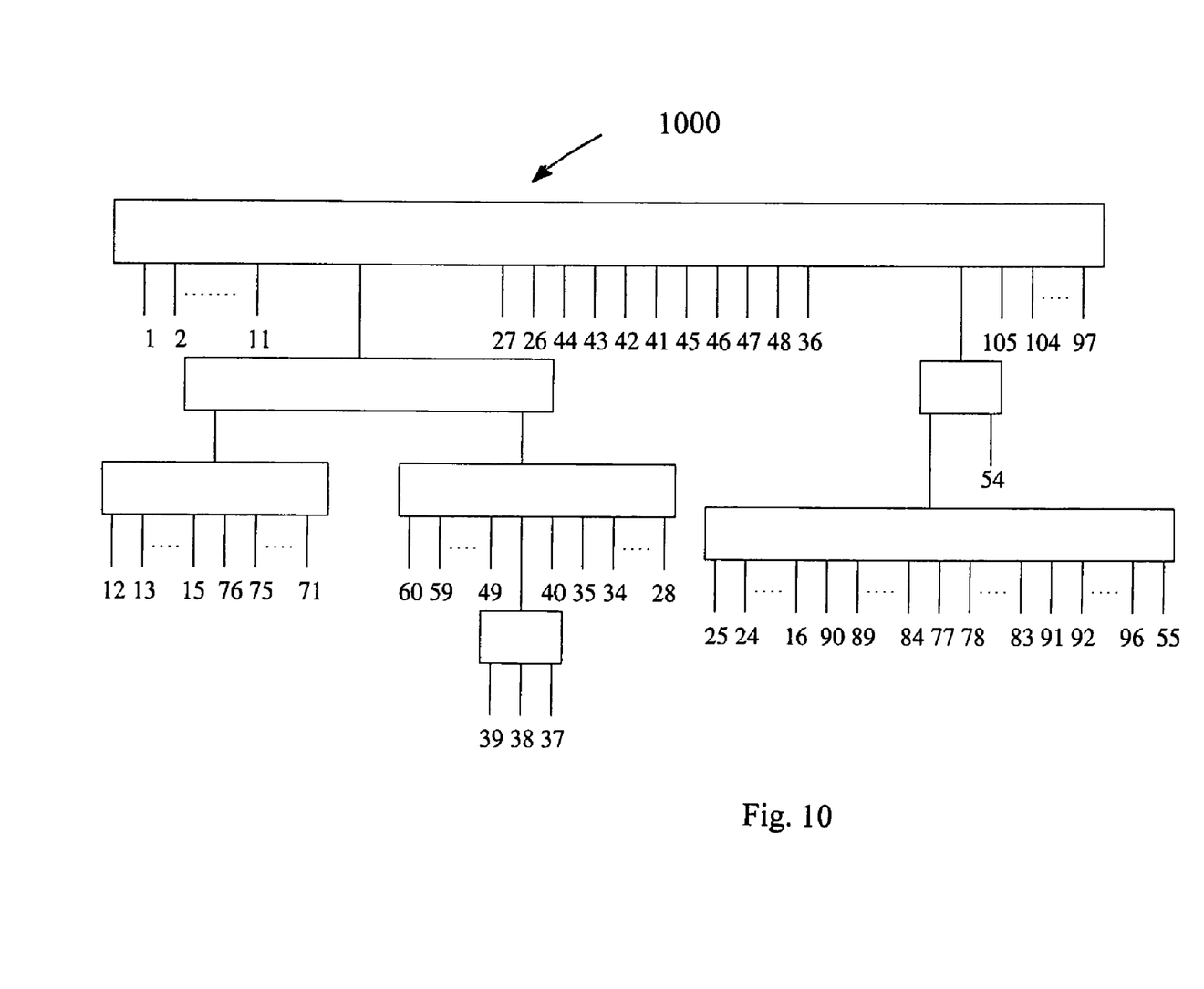
FIG. 10 illustrates a minimal consensus PQ tree 1000 obtained from a comparison between thirteen chloroplast genomes in the flowering plant family Campanulaceae: *Trachelium, Campanula, Adenophora, Symphyandra, Legousia, Asyneuma, Triodanus, Wahlenbergia, Merciera, Codonopsis, Cyananthus, Platycodon*, and Tobacco in accordance with an exemplary embodiment of the present invention.

Notice that this is a π-pattern with multiplicity since genes 54 and 55 appear twice in the π-pattern. This embodiment uses the approach presented above 5 to address the problem of multiplicity. The four different labeling possibilities of genes 54 and 55 in the two appearances of the π-pattern are:

(1) $\pi 1 = (1-15,76-56,55,54,53-49,39-37,40,35-26,44-41, 45-48,36,25-16,90-84,77-83,91-96,55',54', 105-97)$ and $\pi 2 = (1-11,60-56,55,54,53-49,37-40,35-28,12-15,76-61,27-26, 44-41,45-48, 36,54',25-16,90-84,77-83, 91-96,55',105-97)$ (2) $\pi 1 = (1-5,76-56,55,54,53-49,39-37,40,35-26,44-41,45-48,36,25-16,90-84,77-83,91-96,55',54',105-97)$ and $\pi 2 = (1-11,60-56,55,54',53-49,37-40,35-28,12-15,76-61,27-26,44-41,45-48,36,54,25-16,90-84,77-83, 91-96,55',105-97)$ (3) $\pi 1 = (1-15,76-56,55,54,53-49,39-37,40,35-26,44-41, 45-48,36,25-16,90-84,77-83,91-96,55',54',105-97)$ and $\pi 2 = (1-11,60-56,55',54',53-49,37-40,35-28,12-15,76-61,27-26, 44-41,45-48,36,54,25-16,90-84,77-83, 91-96,55,105-97)$ (4) $\pi 1 = (1-15,76-56,55,54,53-49,39-37,40,35-26,44-41, 45-48,36,25-16,90-84,77-83,91-96,55',54',105-97)$ and $\pi 2 = (1-11,60-56,55',54',53-49,37-40,35-28,12-15,76-61,27-26, 44-41,45-48,36,54',25-16,90-84,77-83, 91-96,55,105-97)$ In FIG. 10, only the minimal consensus PQ tree 1000 of the π-pattern is presented. Although, an exemplary embodiment of the present invention built four possible minimal consensus PQ trees for the four different labeling possibilities of genes 54 and 55, the one in FIG. 10 (which corresponds to the first labeling possibility) is the only one that had the smallest $|C(T)|$ and thus is the only minimal consensus PQ tree.

The following presents two PQ trees obtained from a comparison between eight chloroplast genomes in the flowering plant family Campanulaceae. *Trachelium, Symphyandra, Asyneuma, Triodanus, Merciera, Codonopsis, Platycodon*, and Tobacco. An exemplary embodiment of the present invention used only the eight out of the thirteen genome sequences that had no multiplicity (genome model 3). There were 77 maximal permutation patterns out of 6,729 patterns discovered by the present invention.

The following description presents the maximal notation of the π-pattern {1, 2, . . . , 105} that appears in seven out of the eight chloroplast genomes as the following permutations:

In *Trachelium*: (1-15,76-56,53-49,37-40,35-26,44-41,45-48,36,25-16,90-84,77-83,91-96,55-54,105-97).

In *Symphyandra*: (1-15,76-56,39-37,49-53,40,35-26,44-41,45-48, 36,25-16,90-84,77-83,91-96,55-54,105-97).

In *Triodanus*: (1-15,76-56,27-26,44-41,45-48,36-35,25-16,89-84,77-83,90-96,55-53,105-98,28-34,40-37,49-52,97).

In *Merciera*: (1-10,49-53,28-35,40-37,60-56,11-15,76-61, 27-26,44-41,45-48,36,54,25-16,90-85,77-84,91-96,55,105-97).

In *Codonopsis*: (1-8,36-18,15-9,40,56-60,37-39,44-41, 45-53,16-17,54-55,61-76,96-77,105-97).

In *Platycodon*: (1,8,2-5,29-36,56-50,28-26,9,49-45,41-44,37-40,16-25,10-15,57-59,6-7,60-96,105-97).

In Tobacco: (1-105).

The maximal notation of this pattern is (1-((2-3-4-5),(6-7), 8,9,10,(11-12-13-14-15),(76-75-74-73-72-71-70-69-68-67-66-65-64-63-62-61),60,(59-58-57),56,53,(52-51-50),49, (37-38-39),40,35,(34-33-32-31-30-29),28,(27-26),((44-43-42-41)-(45-46-47-48)),36,(25-24-23-22-21-20-19-18),(17-16),((90-((89-88-87-86-85)-(84-(77-78-79-80-81-82-83))))-(91-92-93-94-95-96)),55,54,(105-104-103-102-101-100-99-98),97))

Figure 11:
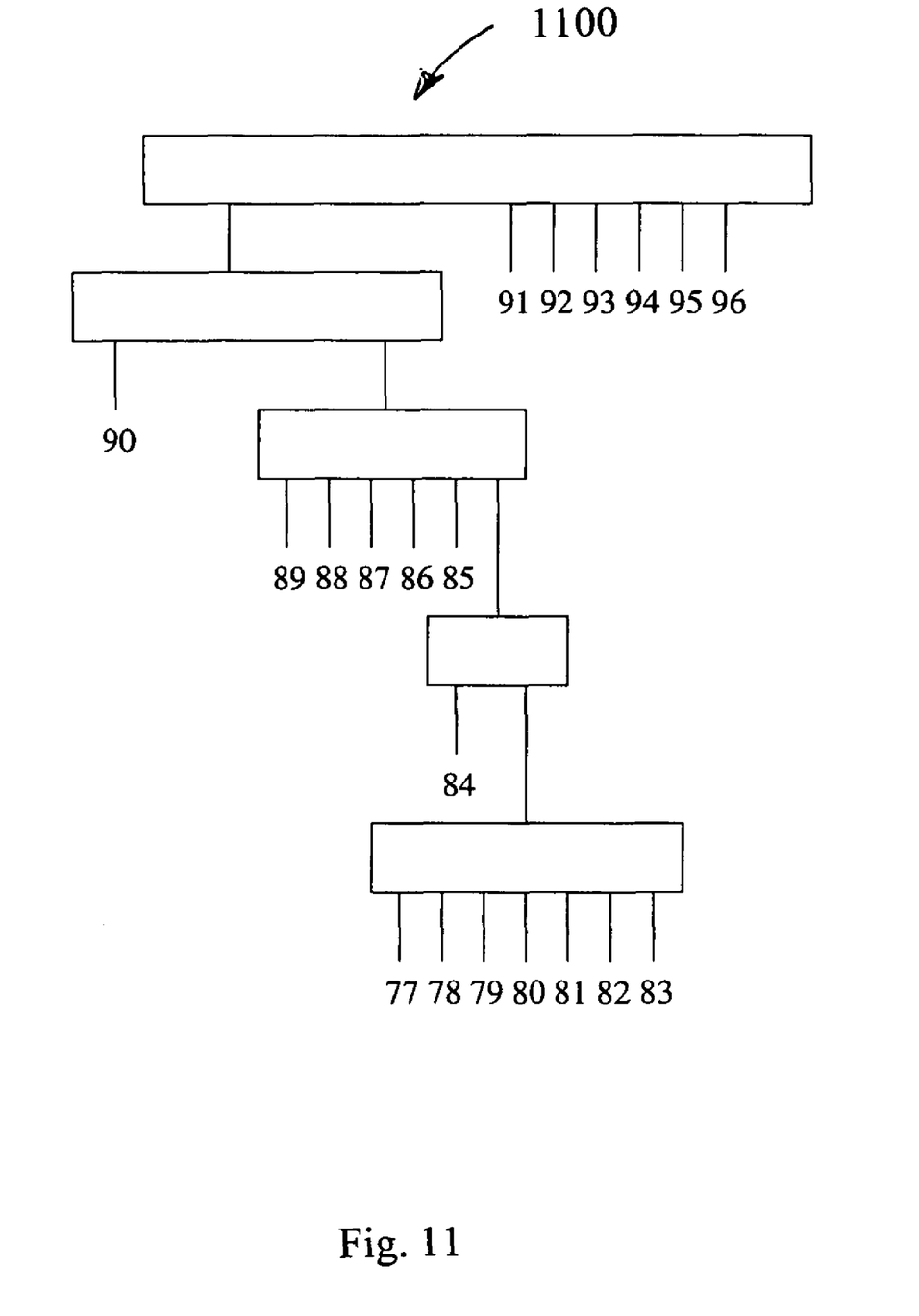
FIG. 11 illustrates another minimal consensus PQ tree 1100 of a π-pattern that appears in all eight chloroplast genomes in accordance with an exemplary embodiment of the present invention.

FIG. 11 presents another minimal consensus PQ tree 1100 of a π-pattern that appears in all eight chloroplast genomes in accordance with an exemplary embodiment of the present invention.

Figure 12:
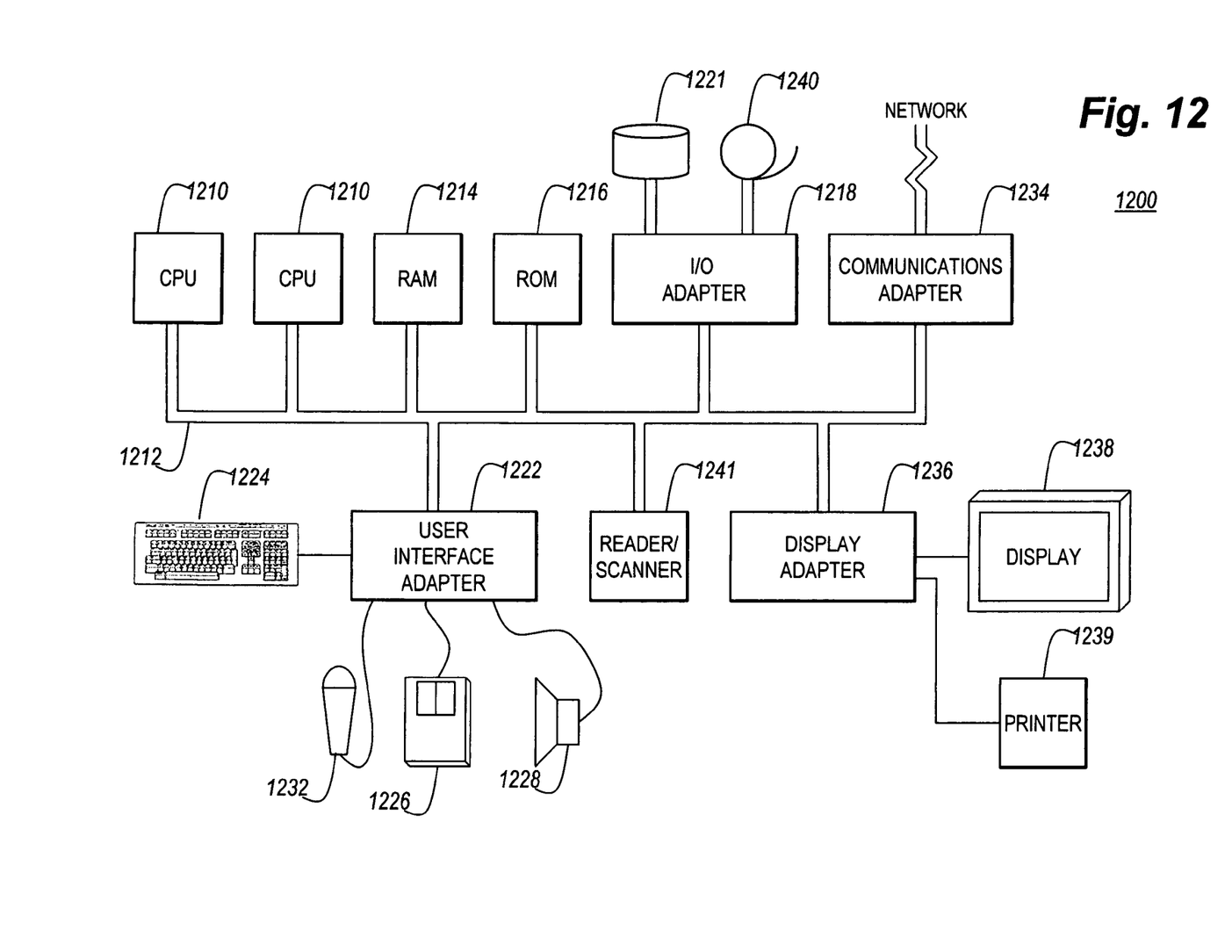
FIG. 12 illustrates an exemplary system 1200 for incorporating the present invention therein.
Figure 13:
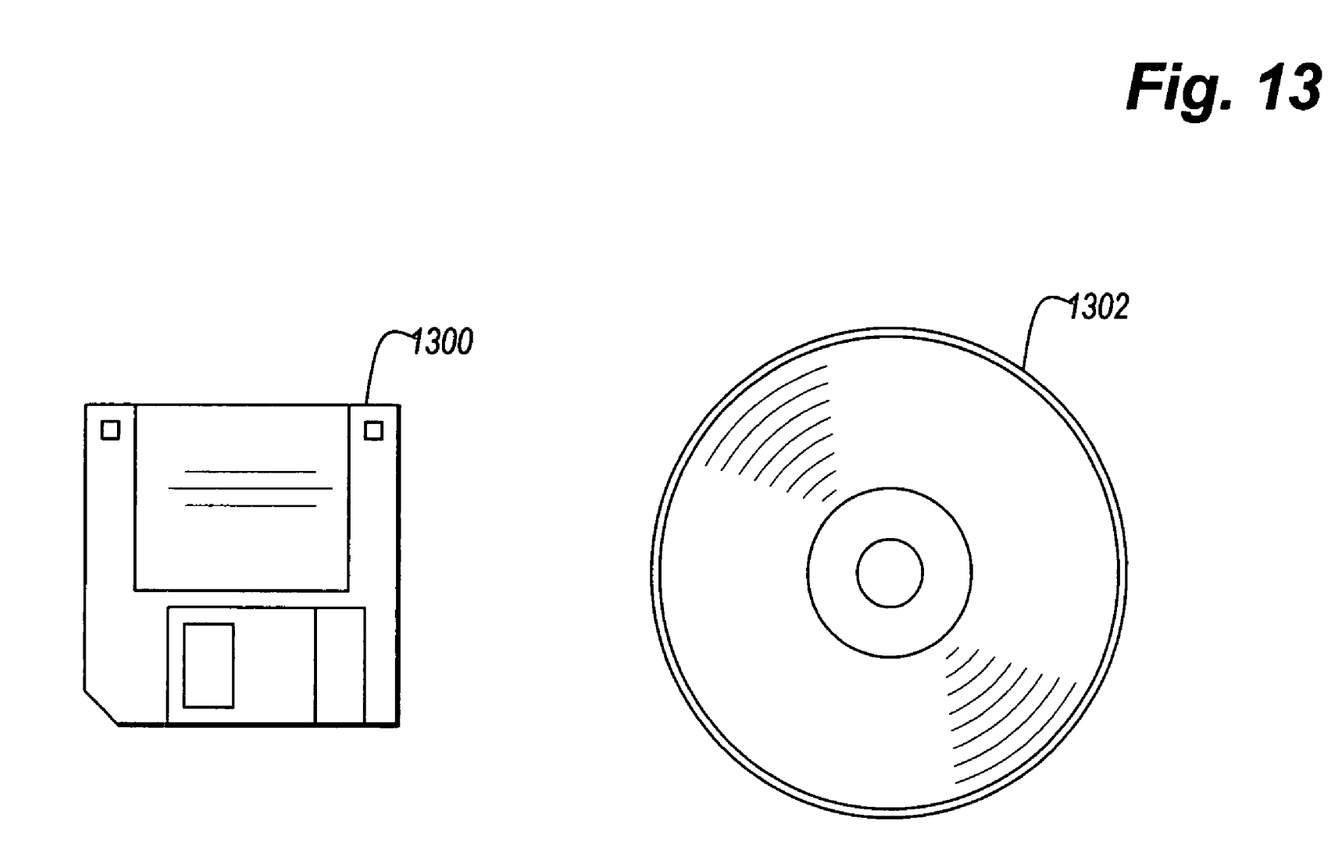
FIG. 13 illustrates a program embodied in a computer readable medium 1300 and 1302 executable by a digital processing unit in accordance with an exemplary method of the present invention.

Referring now to FIG. 12, system 1200 illustrates a typical hardware configuration which may be used for implementing the inventive systems and methods for comparative genomics. The configuration has preferably at least one processor or central processing unit (CPU) 1210. The CPUs 1202 are interconnected via a system bus 1212 to a random access memory (RAM) 1214, read-only memory (ROM) 1216, input/output (I/O) adapter 1218 (for connecting peripheral devices such as disk units 1221 and tape drives 1240 to the bus 1212), user interface adapter 1222 (for connecting a keyboard 1224, mouse 1226, speaker 1228, microphone 1232, and/or other user interface device to the bus 1212), a communication adapter 1234 for connecting an information handling system to a data processing network, the Internet, and Intranet, a personal area network (PAN), etc., and a display adapter 1236 for connecting the bus 1212 to a display device 1238 and/or printer 1239. Further, an automated reader/scanner 1241 may be included. Such readers/scanners are commercially available from many sources.

In addition to the system described above, a different aspect of the invention includes a computer-implemented method for performing the above method. As an example, this method may be implemented in the particular environment discussed above.

Such a method may be implemented, for example, by operating a computer, as embodied by a digital data processing apparatus, to execute a sequence of machine-readable instructions. These instructions may reside in various types of signal-bearing media.

Thus, this aspect of the present invention is directed to a program embodied in a computer readable medium executable by a digital processing unit to perform the above method.

Such a method may be implemented, for example, by operating the CPU 1210 to execute a sequence of machine-readable instructions. These instructions may reside in various types of signal bearing media.

Thus, this aspect of the present invention is directed to a programmed product, comprising signal-bearing media tangibly embodying a program of machine-readable instructions executable by a digital data processor incorporating the CPU 1210 and hardware above, to perform the method of the invention.

This signal-bearing media may include, for example, a RAM contained within the CPU 1210, as represented by the fast-access storage for example. Alternatively, the instructions may be contained in another signal-bearing media, such as a magnetic data storage diskette 1300 or CD-ROM 1302, (FIG. 13), directly or indirectly accessible by the CPU 1210.

Whether contained in the computer server/CPU 1210, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g., CD-ROM, WORM, DVD, digital optical tape, etc.), paper "punch" cards, or other suitable signal-bearing media including transmission media such as digital and analog and communication links and wireless.

In an illustrative embodiment of the invention, the machine-readable instructions may comprise software object code, complied from a language such as "C," etc.

Figure 14:
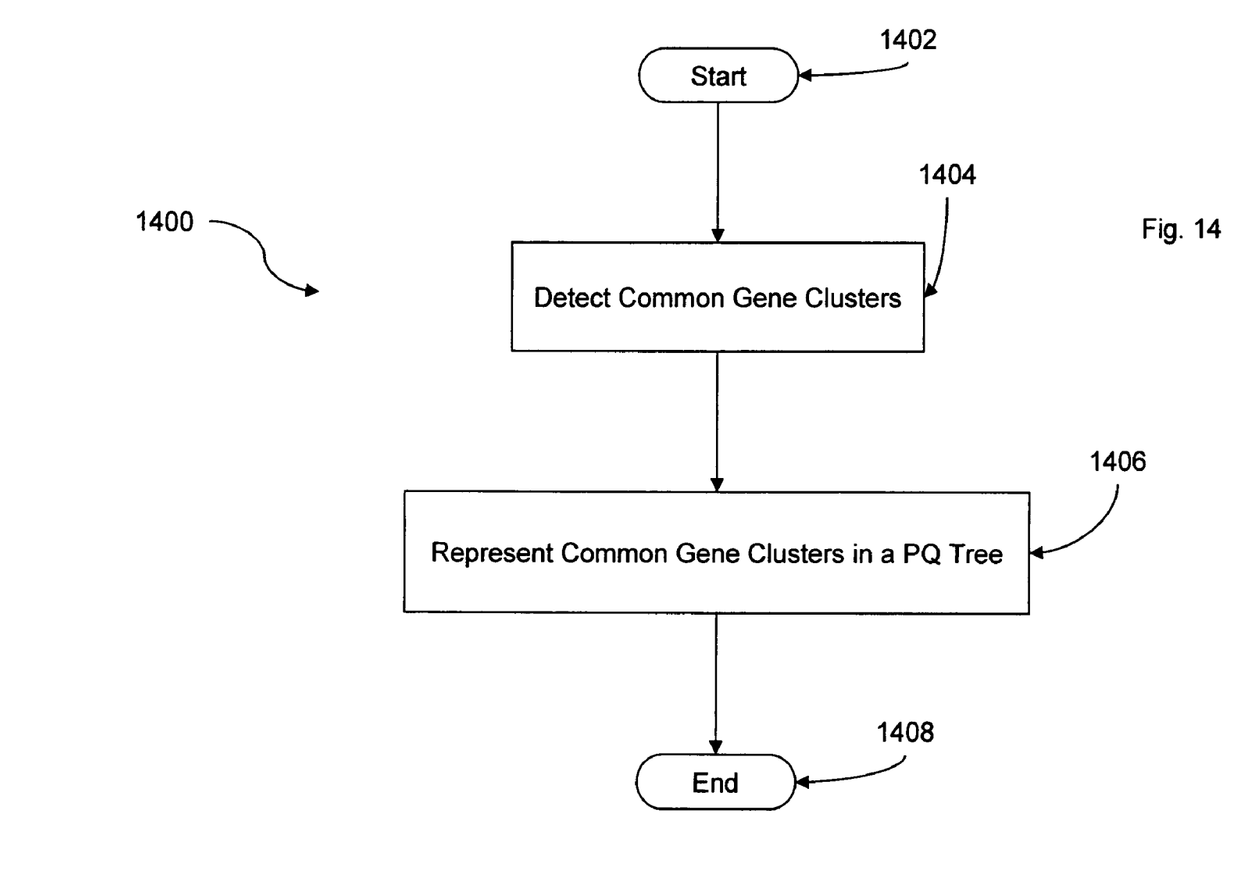
FIG. 14 illustrates a flowchart 1400 in accordance with an exemplary embodiment of the present invention.

FIG. 14 illustrates a flowchart 1400 of an exemplary method in accordance with the present invention. The flowchart starts at step 1402 and continues to step 1404. In step 1404, the flowchart detects gene clusters which are common to at least two genomes and continues to step 1406. In step 1406, the method represents the common gene clusters in a PQ tree and continues to step 1408 where the method ends. Examples of how steps 1404 and 1406 may be performed are described in detail above.

While the invention has been described in terms of several exemplary embodiments, those skilled in the art will recognize that the invention can be practiced with modification.

Further, it is noted that, Applicant's intent is to encompass equivalents of all claim elements, even if amended later during prosecution.

What is claimed is:

1. A method of representing a similarity between at least two genomes, said method comprising:
   detecting gene clusters which are common to said at least two genomes;
   representing said common gene clusters in a PQ tree, as executed by a processing unit on a computer, wherein said PQ tree comprises:
      a first internal node (P node) that allows a permutation of children thereof; and
      a second internal node (Q node) that maintains a unidirectional order of the children thereof; and
   filtering said gene clusters.

2. A method of representing a similarity between at least two genomes, said method comprising:
   detecting gene clusters which are common to said at least two genomes; and
   representing said common gene clusters in a PQ tree, as executed by a processing unit on a computer, wherein said PQ tree comprises:
      a first internal node (P node) that allows a permutation of children thereof; and
      a second internal node (Q node) that maintains a unidirectional order of the children thereof,
   wherein said PQ tree provides a maximal notation of appearances of a pattern in linear time, and
   wherein, given k permutations on an alphabet $\Sigma$, representing k occurrences of a pattern, the maximal notation is obtained by using a '−' between said two genes to denote that these groups appear as immediate neighbors in all the k permutations, and using a ',' otherwise.

3. A method of representing a similarity between at least two genomes, said method comprising:
   detecting gene clusters which are common to said at least two genomes; and
   representing said common gene clusters in a PQ tree, as executed by a processing unit on a computer, wherein said PQ tree comprises:
      a first internal node (P node) that allows a permutation of children thereof; and
      a second internal node (Q node) that maintains a unidirectional order of the children thereof,
   wherein said PQ tree provides a maximal notation of appearances of a pattern in linear time, and
   wherein a maximal notation of a $\pi$-pattern p in $O(nk^2)$ time is obtained, where k is a number of appearances of p and n is a number of characters in p, and $O(nk^2)$ is time proportional to n times $k^2$ with a constant of proportionality c such that $c \ll n$ and $c \ll k$.

4. A method of representing a similarity between at least two genomes, said method comprising:
   detecting gene clusters which are common to said at least two genomes;
   representing said common gene clusters in a PQ tree, as executed by a processing unit on a computer, wherein said PQ tree comprises:
      a first internal node (P node) that allows a permutation of children thereof; and
      a second internal node (Q node) that maintains a unidirectional order of the children thereof; and solving a general consecutive arrangement problem using said PQ tree, wherein said general consecutive arrangement problem is solved using said PQ tree and an algorithm $O(n^2)$, where n is a number of characters in input and $O(n^2)$ is time proportional to $n^2$ with a constant of proportionality c such that $c \ll n$.

5. A system for representing a similarity between at least two genomes, said system comprising:

a detector that detects gene clusters which are common to said at least two genomes;

a processor that represents said common gene clusters in a PQ tree, wherein said PQ tree comprises:

a first internal node (P node) that allows a permutation of children thereof; and a second internal node (Q node) that maintains a unidirectional order of the children thereof; and a filter that filters said gene clusters.

6. A system for representing a similarity between at least two genomes, said system comprising:

a detector that detects gene clusters which are common to said at least two genomes; and a processor that represents said common gene clusters in a PQ tree, wherein said PQ tree comprises:

a first internal node (P node) that allows a permutation of children thereof; and a second internal node (Q node) that maintains a unidirectional order of the children thereof;

wherein said PQ tree provides a maximal notation of the appearances of a pattern in linear time, and wherein, given k permutations on an alphabet $\Sigma$, representing k occurrences of a pattern, the maximal notation is obtained by using a '–' between said two genes to denote that these groups appear as immediate neighbors in all the k permutations, and using a ',' otherwise.

7. A system for representing a similarity between at least two genomes, said system comprising:

a detector that detects gene clusters which are common to said at least two genomes; and a processor that represents said common gene clusters in a PQ tree, wherein said PQ tree comprises:

a first internal node (P node) that allows a permutation of children thereof; and a second internal node (Q node) that maintains a unidirectional order of the children thereof;

wherein said processor solves a general consecutive arrangement problem using said PQ tree, and wherein said general consecutive arrangement problem is solved using said PQ tree and an algorithm $O(n^2)$, where n is a number of characters in input and $O(n^2)$ is time proportional to $n^2$ with a constant of proportionality c such that $c \ll n$ and $c \ll k$.

* * * * *